United States Patent [19]

Yoon

[11] Patent Number: 5,549,564
[45] Date of Patent: * Aug. 27, 1996

[54] SAFETY PENETRATING INSTRUMENT

[76] Inventor: InBae Yoon, 2101 Highland Ridge Dr., Phoenix, Md. 21131

[*] Notice: The portion of the term of this patent subsequent to Jul. 13, 2010, has been disclaimed.

[21] Appl. No.: 71,888

[22] Filed: Jun. 7, 1993

Related U.S. Application Data

[63] Continuation of Ser. No. 628,899, Dec. 18, 1990, Pat. No. 5,226,426.

[51] Int. Cl.⁶ ................................. A61B 10/00
[52] U.S. Cl. .................... 604/165; 604/164; 606/185
[58] Field of Search ......................... 128/751, 752, 128/753, 754, 4; 604/95, 158, 162, 163, 164, 165, 170, 272, 274, 280, 51, 169, 264; 606/185, 167, 171

[56] References Cited

U.S. PATENT DOCUMENTS

| | | | |
|---|---|---|---|
| 1,087,845 | 2/1914 | Stevens | 604/159 |
| 1,147,408 | 7/1915 | Kells | 604/164 |
| 1,213,001 | 1/1917 | Philips | 604/165 |
| 1,248,492 | 12/1917 | Hill | 604/165 |
| 1,527,291 | 2/1925 | Zorraquin | 604/158 |
| 1,835,287 | 12/1931 | Donovan | 604/275 |
| 2,389,355 | 11/1945 | Goland et al. | 604/165 |
| 2,496,111 | 1/1950 | Turkel | 128/754 |
| 2,541,542 | 2/1951 | Perez et al. | 128/754 |
| 2,623,521 | 12/1952 | Shaw | 604/170 |
| 2,630,803 | 3/1953 | Baran | 604/158 |
| 3,540,447 | 11/1970 | Howe | 604/165 |
| 3,545,443 | 12/1970 | Ansari | 604/160 |
| 3,565,074 | 2/1971 | Foti | 604/164 |
| 3,817,250 | 6/1974 | Weiss et al. | 128/207.29 |
| 3,860,006 | 1/1975 | Patel | 604/164 |
| 3,895,632 | 7/1975 | Plowiecki | 604/169 |
| 3,993,079 | 11/1976 | Gatztanondo . | |
| 3,994,287 | 11/1976 | Turp et al. . | |
| 4,013,080 | 3/1977 | Froning . | |
| 4,144,884 | 3/1979 | Tersteegen et al. . | |
| 4,163,446 | 8/1979 | Jamshidi . | |
| 4,177,814 | 12/1979 | Knepshield et al. . | |
| 4,254,762 | 3/1981 | Yoon . | |
| 4,345,589 | 8/1982 | Hiltebrandt . | |
| 4,379,458 | 4/1983 | Bauer et al. . | |
| 4,396,021 | 8/1983 | Baumgartner . | |
| 4,513,754 | 4/1985 | Lee . | |
| 4,535,773 | 8/1985 | Yoon . | |
| 4,601,710 | 7/1986 | Moll . | |
| 4,609,370 | 9/1986 | Morrison . | |
| 4,654,030 | 3/1987 | Moll et al. . | |
| 4,702,261 | 10/1987 | Cornell et al. . | |
| 4,733,671 | 3/1988 | Mehl . | |
| 4,828,547 | 5/1989 | Sahi et al. . | |

(List continued on next page.)

FOREIGN PATENT DOCUMENTS

| | | |
|---|---|---|
| 2544262 | 4/1977 | Germany . |
| 878265 | 11/1981 | U.S.S.R. . |
| 897224 | 1/1982 | U.S.S.R. . |
| 904635 | 8/1962 | United Kingdom . |

*Primary Examiner*—Guy V. Tucker

[57] ABSTRACT

The safety penetrating instrument includes a tubular needle having a distal end with a sharp tip, a safety probe movable within the needle between an extended position protecting the needle tip and a retracted position exposing the needle tip and is biased toward the extended position and a portal sleeve surrounding the needle to establish communication with an anatomical cavity with penetration of tissue surrounding the cavity by the needle. The needle distal end has a leading edge defining the sharp tip and a trailing edge and the portal sleeve has a distal edge disposed in substantial alignment with or forward of the trailing edge of the needle distal end. A locking mechanism automatically locks the safety probe in the extended position after the safety probe is returned thereto or can optionally allow locking of the safety probe or allow proximal movement of the safety probe after return to the extended position. The locking mechanism also provides selective locking of the safety probe in the retracted position.

11 Claims, 2 Drawing Sheets

U.S. PATENT DOCUMENTS

| | | |
|---|---|---|
| 4,869,717 | 9/1989 | Adair . |
| 4,902,280 | 2/1990 | Lander . |
| 4,926,877 | 5/1990 | Bookwalter . |
| 4,931,042 | 6/1990 | Holmes et al. . |
| 5,030,206 | 7/1991 | Lander . |
| 5,066,288 | 11/1991 | Deniega et al. . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,127,909 | 7/1992 | Shichman . |
| 5,226,426 | 7/1993 | Yoon ........................................ 128/753 |
| 5,318,580 | 6/1994 | Gresl, Jr. .................................. 606/185 |

SAFETY PENETRATING INSTRUMENT

This application is a continuation of application Ser. No. 07/628,899 filed Dec. 18, 1990, now U.S. Pat. No. 5,226,426.

BACKGROUND OF THE INVENTION

1. Field of the Invention

The present invention pertains to surgical penetrating instruments and, more particularly, to safety surgical penetrating instruments having tubular needles for penetrating tissue and safety probes for protecting the sharp tips of the needles.

2. Discussion of the Prior Art

Surgical penetrating instruments are widely used in surgical procedures to gain access to anatomical cavities ranging in size from the abdomen to small blood vessels, such as veins and arteries, epidural, pleural and subarachnoid spaces, heart ventricles and spinal and synovial cavities. Such surgical penetrating instruments include a penetrating member or implement having a sharp tip or point to pierce or penetrate the tissue forming the cavity wall, and the force required to penetrate the cavity wall is dependent upon the type and thickness of the tissue of the wall. Once the wall is penetrated, it is desirable to protect the sharp tip of the penetrating member to prevent inadvertent contact with tissue in or forming the cavity, and a particular problem exists where substantial force is required to penetrate the cavity wall in that, once penetration is achieved, the lack of tissue resistance can result in the sharp tip travelling too far into the cavity and injuring adjacent tissue.

Safety penetrating instruments including a safety probe biased to extend beyond the sharp tip of a penetrating member have become widely accepted for use in penetrating anatomical cavities. For example, the Verres needle, commonly used to create a pneumoperitoneum, has a spring-loaded inner member disposed within a tubular needle. U.S. Pat. Nos. 1,527,291 to Zorraquin, No. 2,623,521 to Shaw and No. 2,630,803 to Baran are exemplary of safety penetrating instruments with a spring-loaded inner member disposed in a needle, while U.S. Pat. No. 4,254,762 to Yoon shows an endoscope spring-biased in a hollow needle. Safety trocars having a spring-biased protective shield disposed between an outer sleeve and an inner trocar are marketed by Ethicon, Inc. as the Endopath and by United States Surgical Corp. as the Surgiport. U.S. Pat. Nos. 4,535,773 to Yoon No. 4,601,710 to Moll and No. 4,654,030 to Moll et al are exemplary of such safety trocars. German Offenlegungsschrift 2,544,262 discloses an intrauterine catheter including a tube having a distal sharp point, a spring-biased blunt member in the tube distal end and a hose or catheter slidable over the tube.

While the prior art safety penetrating instruments are widely used, they suffer from many disadvantages when used in the procedures for which they are presently recommended; and, additionally, prior art safety penetrating instruments cannot be used in many procedures for which safety of penetration is highly desirable. One of the disadvantages of prior art surgical penetrating instruments is that, when the penetrating member is a tubular needle with an acutely angled distal end, the sharp tip is not well protected and is still at least partially exposed when the safety probe is extended to the protective position such that use in penetrating small of narrow anatomical cavities is not safe, while another disadvantage is that the safety probe cannot be locked in an extended, needle tip protecting position. A further disadvantage is that the sharp tip of the needle cannot be selectively exposed for effective use in further penetration of tissue after a cavity wall is initially penetrated.

SUMMARY OF THE INVENTION

Accordingly, it is a primary object of the present invention to overcome the above mentioned disadvantages of the prior art by utilizing a tubular needle with a safety probe movable therein in a safety penetrating instrument including a portal sleeve thereby increasing safety and efficacy in a wide range of surgical procedures.

Another object of the present invention is to position the distal edge of a portal sleeve in alignment with or forward of the trailing edge of an angled open end of a needle in a safety penetrating instrument having a safety probe movable in the needle such that the needle and portal sleeve present a substantially smooth profile for tissue penetration.

A further object is to optionally allow locking of a safety probe in an extended position in a needle of a safety penetrating instrument including a portal sleeve or to allow the safety probe to move proximally from the extended position.

Another object of the present invention is to utilize a tubular needle to position a portal sleeve through a cavity wall with the sharp tip of the needle received in a protective recess in a safety probe to minimize exposure of the sharp tip both after penetration of tissue and during handling by medical personnel thereby reducing the opportunity for contact and/or piercing of tissue inadvertently.

A further object of the present invention is to align an angled distal end surface of a safety probe with an angled sharp distal end of a tubular needle within a portal sleeve such that the distal ends of the safety probe and the needle are in substantially the same plane during tissue penetration to facilitate placement of the portal sleeve.

An additional object of the present invention is to utilize a safety probe in a tubular needle having an open distal end with a portion curving toward the longitudinal axis of the needle to terminate at a sharp tip such that, in an extended position, the distal end of the safety probe protrudes over the sharp tip of the needle.

The present invention has another object in that a safety probe movable relative to an elongate penetrating needle within a portal sleeve is biased toward an extended position and can be selectively, releasably locked in a retracted position such that the safety probe can be disabled prior to or after penetration of a cavity wall.

Yet another object of the present invention is to construct a safety penetrating instrument such that a distally biased safety probe can be manually pulled proximally toward a retracted position to expose the sharp distal end of a tubular needle without requiring a force applied to the distal end of the safety probe from tissue contact.

A further object of the present invention is to utilize a safety probe having an expandable distal end in a safety penetrating instrument including a portal sleeve such that in an extended position the distal end of the safety probe is in an expanded state protecting the sharp tip of a tubular needle while in a retracted position the distal end of the safety probe is in a contracted state substantially filling the needle. The distal end of the safety probe can be slotted or split to permit further use for grasping tissue, such as for biopsy.

The present invention has an additional object in the use of a pin and slot mechanism to provide selective locking of a safety probe distally biased relative to a penetrating needle, the pin extending externally of a hub to form a handle graspable by a surgeon to selectively move the safety probe. When the pin is in a longitudinal portion of the slot, the safety probe can be moved against the bias; and, when the pin is in proximal or distal transverse portions of the slot at opposite ends of the longitudinal portion, the safety probe is releasably locked in retracted and extended positions, respectively.

Some of the advantages of the present invention over the prior art are that very small cavities, such as veins, arteries, pleural spaces, spinal canals and subarachnoid and epidural spaces, can be safely penetrated to establish a portal in communication therewith, the chance of developing a hematoma during penetration of a vein or artery is substantially reduced, second puncture endoscopic procedures are facilitated, safe penetration is achieved while permitting injection or evacuation of fluids, penetration into additional tissue after penetration of a cavity wall can be accomplished with a single instrument, such as into a cystic cavity or soft organ structure (e.g., ovarian cyst penetration or liver tissue biopsy), a single puncture can be used for both insufflation and forming an endoscopic portal thereby simplifying procedures such as laparoscopies, and safety penetrating instruments according to the present invention can be inexpensively manufactured to permit universal use in place of presently used penetrating members, such as trocars and tubular needles.

The present invention is generally characterized in a safety penetrating instrument including a tubular needle having a distal end with a sharp tip, a safety probe movable within the needle between an extended position protecting the needle tip and a retracted position exposing the needle tip and biased toward the extended position, a hub receiving the proximal ends of the needle and the safety probe, and a portal sleeve surrounding the needle to establish communication with an anatomical cavity with penetration by the needle. The needle distal end has a leading edge defining the sharp tip and a trailing edge, and the distal edge of the portal sleeve is disposed in substantial alignment with or forward of the trailing edge of the needle distal end. A locking mechanism automatically locks the safety probe in the extended position after the safety probe is returned hereto or can optionally allow locking of the safety probe or allow proximal movement of the safety probe after return to the extended position. The locking mechanism also provides selective locking of the safety probe in the retracted position. The distal end of the safety probe has an angled end surface such that, in the retracted position, the angled end surface of the safety probe is in substantially the same plane as the angled distal peripheral edge of the needle.

Other objects and advantages of the present invention will become apparent from the following description of the preferred embodiments taken in conjunction with the accompanying drawings wherein like parts in each of the several figures are identified by the same reference characters.

DESCRIPTION OF THE PREFERRED EMBODIMENTS

Figures 1, 2, 3:
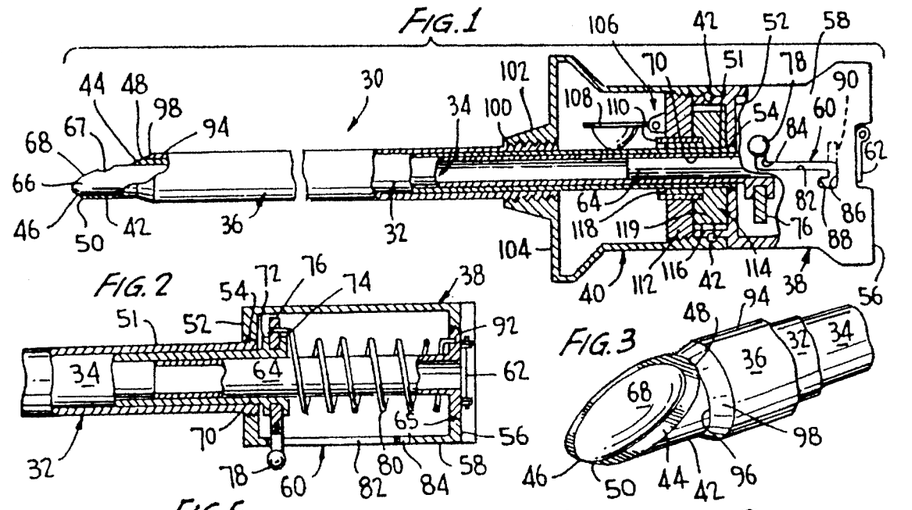
FIG. 1 is a broken side view, partly in section, of a safety penetrating instrument according to the present invention.
FIG. 2 is a broken view partly in section, of the hub and locking mechanism.
FIG. 3 is a broken perspective view of the distal end of the safety penetrating instrument of FIG. 1 in a retracted position.

A safety penetrating instrument 30 according to the present invention is illustrated in FIG. 1 and includes an elongate, tubular needle 32, a safety probe 34 movably disposed concentrically within needle 32, an elongate, tubular portal sleeve 36 concentrically disposed around needle 32, a hub 38 mounting needle 32 and safety probe 34 and a housing 40 mounting portal sleeve 36. The hub 38 can be latched to housing 40 with the use of any suitable releasable mechanism, such as ball detents 41, allowing the hub to be removed from the housing withdrawing the needle and safety probe from the portal sleeve. Accordingly, the safety penetrating instrument 30 may be considered to be formed of a portal unit and a penetrating unit, the portal unit including portal sleeve 36 and housing 40 and the penetrating unit including needle 32, safety probe 34 and hub 38.

Needle 32 is preferably made of a cylindrical length of stainless steel having a diameter and wall thickness dependent upon the procedure to be performed and the anatomical cavity to be penetrated. The needle has a distal end 42 terminating at a peripheral edge 44 disposed in a plane positioned at an acute angle relative to the longitudinal axis of the needle to define a sharp, tissue penetrating tip or point 46 at a leading or front edge and, proximally spaced from the leading edge, a trailing or rear edge 48. At the leading edge, the wall of the needle is ground at an angle, as shown at 50, to terminate at sharp tip 46 such that tip 46 is aligned with the inner surface of the cylindrical needle wall. Needle 32 has a proximal end 51 secured to a front wall 52 of hub 38 by any suitable means, such as threads 54 or cement.

Hub 38 is preferably made of plastic to reduce cost and has an external configuration to cooperate with housing 40 to be easily grasped with one hand for use in penetrating tissue. Hub 38 is substantially rectangular in cross-section and includes, as best shown in FIGS. 1 and 2, four side walls extending from front wall 52 to a rear wall 56 to provide a rearwardly flared outer profile with one side wall, indicated at 58, having a slot 60 therein. Rear wall 56 has a recess therein receiving and protecting a valve 62 which is shown as a flap valve but could be any type of valve, such as a stop cock. A tube 64 has a flange 65 threadedly secured to rear wall 56 adjacent valve 62 such that valve 62 controls flow therethrough, and tube 64 extends through hub 38 to be slidably received in safety probe 34.

Safety probe 34 is preferably made from a cylindrical length of a rigid or flexible material, such as stainless steel or plastic dependent upon use of the safety penetrating instrument, and has a distal end 66 with a configuration to protect sharp tip 46 of needle 32 in an extended position as shown in FIG. 1. The distal end 66 has a hole 67 therein and an end surface 68 disposed at an acute angle to the longitudinal axis of needle 32 substantially the same as the acute angle of the needle peripheral edge 44. In this manner, the peripheral edge 44 of the distal end of needle 32 and the distal end surface 68 of safety probe 34 will be maintained in substantially parallel relation when the safety probe is in the extended position and will be positioned in substantially the same plane when the safety probe is in the retracted position as illustrated in FIG. 3. End surface 68 has a rounded, partially spherical or bulging, dome-shaped configuration; however, dependent upon use of the safety penetrating instrument, the end surface can be substantially flat so long as sharp surfaces are avoided. By grinding the distal end of the needle, the sharp tip 46 is positioned in abutment with the lateral wall of the safety probe in the extended position to be well protected and unexposed. As best shown in FIG. 2, the safety probe has a proximal end 70 disposed within hub 38 carrying spaced annular ribs 72 and 74 between which is rotatably mounted a member or plate 76 having a pin 78 threadedly secured thereto and extending through slot 60, the pin 78 having a spherical end or knob to be easily grasped. A helical spring 80 is mounted in compression between plate 76 and the end wall of hub 38, and the spring 80 has longitudinally extending ends received in apertures in plate 76 and flange 65 such that the spring can be wound in torsion to bias the plate and the pin 78 carried thereby in a clockwise direction looking at the proximal end of the safety penetration instrument or upwardly looking at FIG. 1. The slot 60 formed in hub 38 has a longitudinal portion 82 aligned in parallel relation with the longitudinal axis of the needle, a distal transverse portion 84 and a proximal transverse portion 86 having a recess 88 at the end thereof extending parallel with the longitudinal slot portion 82. If desired, for purposes to be explained hereinafter, the proximal slot portion can extend in the same direction as the distal slot portion as shown in dashed lines at 90.

Figures 19, 20, 21:
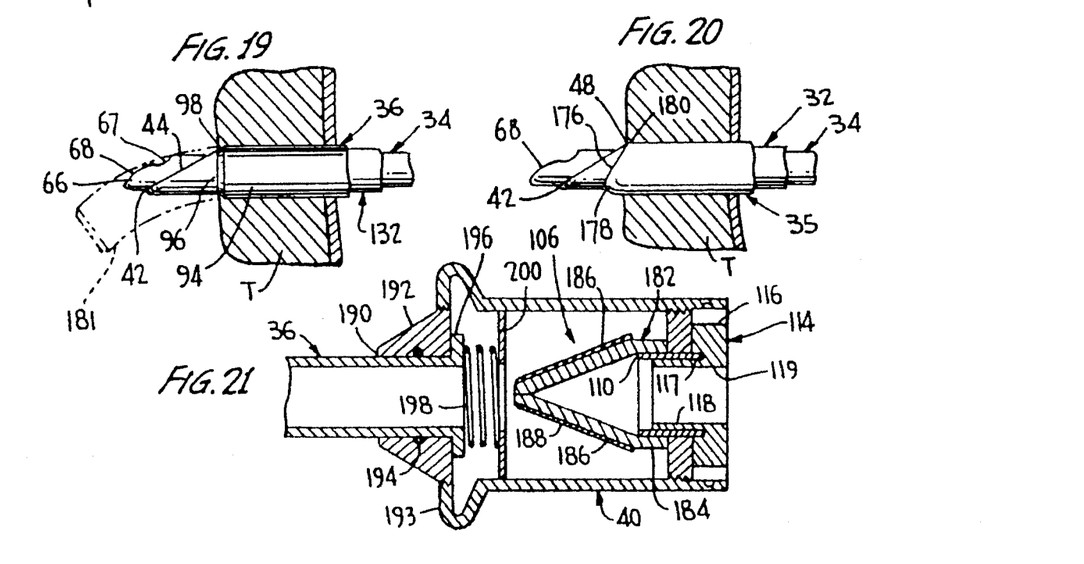
FIG. 20 is a broken view of a modification of the portal sleeve of the safety penetrating instrument according to the present invention.
FIG. 21 is a broken sectional view of a modification of the safety penetrating instrument according to the present invention.

Portal sleeve 36 is preferably made of a cylindrical length of stainless steel or other suitable, medically acceptable, plastic or metal material and can be rigid or flexible and transparent or opaque. The portal sleeve has a distal end 94 terminating at a peripheral edge 96 disposed in substantial alignment with or forward of the trailing edge 48 of the needle such that the distal ends of the needle and the portal sleeve present a substantially smooth profile to facilitate tissue penetration. The distal end 94 has a tapered, conical portion 98 disposed at the same acute angle to the longitudinal axis of needle 32 as the angle of the peripheral edge 44 of the needle such that the portal sleeve 36 smoothly follows the needle during tissue penetration. The portal sleeve 36 has a threaded proximal end 100 removably received in a threaded nipple 102 extending from a front wall 104 of housing 40. Housing 40 is preferably made of plastic and has a rectangular configuration in cross-section corresponding to the cross-sectional configuration of hub 38 with a flared external profile adjacent front wall 104 to facilitate grasping during use. A valve assembly 106 is mounted in housing 40 to control flow through the portal sleeve once the penetrating unit is removed therefrom. The valve assembly can have any acceptable configuration and, as shown, includes a flapper valve member 108 spring-biased to a closed position against an annular valve seat formed by the distal end of a cylindrical tube 110 secured in a threaded plate 112 pivotally mounting the valve member and threadedly secured in an annular threaded wall portion of housing 40. An adapter plug 114 is mounted on the proximal end of tube 110 and is integrally constructed of a flexible resilient material, such as Teflon, silicone rubber or plastic. The adapter plug 114, as also shown in FIG. 21, has a thick flange portion 116 with an annular recess 117 therein for receiving the proximal end of tube 110 and a cylindrical inner wall 118 extending from an inner edge of a central aperture 119 in the flange 116 to be snugly received within tube 110. The thickness of wall 118 is dependent upon the size of the instrument to be inserted through the portal sleeve such that, if instruments smaller than the penetrating unit are to be introduced into the body after the penetrating unit is withdrawn from the portal sleeve, the adapter plug 114 is removed from the proximal end of tube 110 and another adapter sleeve is inserted therefor having an inner cylindrical wall of greater thickness to engage the smaller instruments along the length of the wall. That is, the diameter of the inner wall 118 and the thickness thereof will vary dependent upon the diameter of instruments passing through the portal unit, and the inner diameter will be substantially the same as or slightly less than the outer diameter of the instrument passing therethrough to produce a seal there-around extending along the length of the wall. By utilizing various size adapter plugs with inner sealing walls to accommodate various size instruments, an effective seal can be produced for instruments varying greatly in size, for example from 2 mm to 12 mm.

In order to assemble the safety penetrating instrument 30, the safety probe 34 can be inserted in the proximal end of the hub and through the needle along with the tube 80 and spring 80. With the plate 76 in place, the pin 78 is passed through the slot 60 and screwed into the plate such that the plate cannot rotate within the hub. The tube 64 is twisted clockwise to create torsion in the spring to rotationally bias plate 76 and pin 78 clockwise as noted above. The tube flange 65 is then screwed into the end wall 56 of the hub to place the safety penetrating instrument 30 in the condition shown in FIG. 2 with spring 80 biasing the safety probe distally such that the distal end 66 is normally in the extended position shown in FIG. 1 protecting the sharp tip 46 of the needle. The pin 78 will be, accordingly, biased distally along longitudinal portion 82 of slot 60 to a position adjacent distal transverse portion 84 and be biased into transverse slot portion 84 due to the torsional bias from the spring to releasably lock the safety probe in the extended position. The penetrating unit formed by the needle 32, the safety probe 34 and the hub 38 is then combined with the portal unit by passing needle 32 through the central aperture in adapter plug 114 and through housing 40 and portal sleeve 36 moving valve member 108 away from the valve seat on the distal end of tube 110. With the hub 38 abutting the housing 40, a cylindrical skirt 119 extending from hub front wall 52 will be disposed within the open proximal end of the housing, and the detents 42 will hold the hub in position with respect to the housing. In this position, the distal peripheral edge 96 will be disposed substantially in alignment with the trailing edge 48 of the needle distal end to facilitate tissue penetration by the safety penetrating instrument 30. It is important for smooth tissue penetration that the distal end of the portal sleeve be positioned at least in alignment with the trailing edge of the needle or forward thereof. If the distal end of the portal sleeve is proximally spaced from the trailing edge of the needle, tissue penetration will be more difficult with increased trauma. Accordingly, the positioning of the distal ends of the needle, the safety probe and the portal sleeve are extremely important in facilitating tissue penetration with minimal tissue resistance and trauma.

The distal end of the safety penetrating instrument 30 is illustrated in FIG. 3 with the safety probe in the retracted position, and it can be seen therefrom that the end surface 68 of the distal end of the safety probe is in substantially the same plane as the peripheral edge 44 at the distal end 42 of the needle 32 with the distal end of the safety probe substantially filling the open distal end of the needle to reduce gaps between the distal ends of the needle and the safety probe and the trapping or jamming of tissue therebetween.

Figure 4:
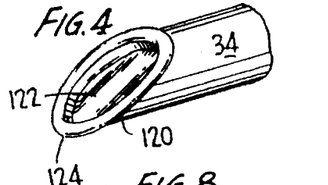
FIG. 4 is a broken perspective view of a modification of the distal end of the safety according to the present invention.

A modification of the safety probe 34 is illustrated in FIG. 4 wherein the safety probe has a distal end 120 having an end surface 122 angled similar to end surface 68 in FIG. 3. A protruding peripheral rim 124 extends from end surface 122 to expand laterally in all directions when the safety probe is in the extended position and contract to completely fill the open distal end of the needle when the safety probe is in the retracted position. In this manner, the reduced gaps between the distal ends of the needle and safety probe in the embodiment of FIG. 3 are prevented to eliminate trapping or jamming of tissue.

Figure 5:
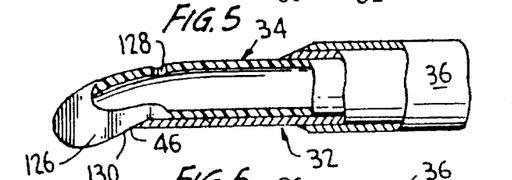
FIG. 5 is a broken side view, partly in section, of another modification of the distal end of the safety penetrating instrument according to the present invention.
Figure 6:
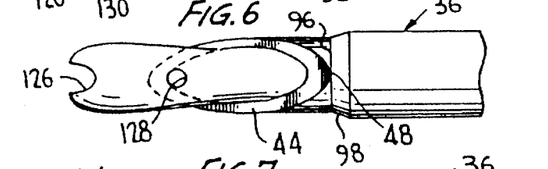
FIGS. 6, 7 and 8 are broken top, bottom and end views, respectively, of the safety penetrating instrument of FIG. 5.
Figure 7:
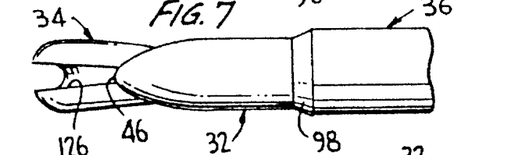
Figure 8:
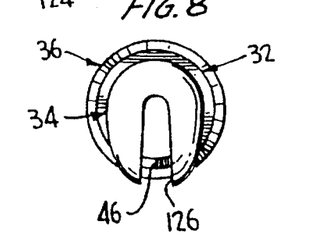

A modification of safety penetrating instrument 30 is illustrated in FIGS. 5, 6, 7 and 8 with the primary differences being that the sharp point 46 at the distal end of the needle 32 is not angularly ground such that the sharp tip is aligned with the outer surface of the wall of the needle as in conventional hypodermic needles and that the safety probe 34 has a groove or recess 126 formed therein such that the distal end is closed with the exception of a lateral hole 128. The distal end of the safety probe has a specific configuration to protect the sharp needle tip 46 due to the needle tip being received in groove 126 when the safety probe is in the extended position and further due to the distal end being bent or angled, as best shown in FIG. 5, relative to the longitudinal axis of the needle such that, in the extended position, the bent portion forms a second recess 130 for receiving the sharp needle tip 46. By constructing the safety probe of a flexible material, such as plastic, the safety probe will straighten or realign when moved, to the retracted position and, when moved to the extended position, will return to the bent or angled configuration forming recess 130 for receiving the needle tip.

Figure 9:
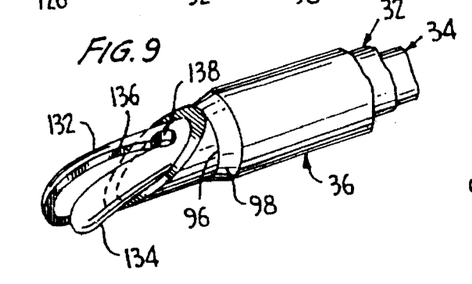
FIGS. 9 and 10 are broken views of a further modification of the distal end of the safety penetrating instrument according to the present invention in extended and retracted positions respectively.
Figure 10:
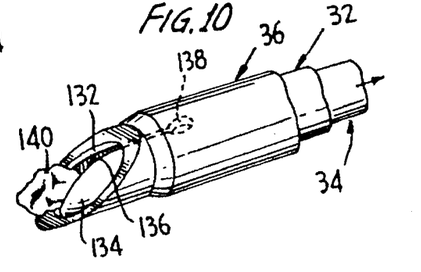

In a further embodiment illustrated in FIG. 9, the distal end of the safety probe is angled or bent as described with respect to the previous embodiment and, additionally, the distal end is split or slotted to form opposing parts 132 and 134. The split or slot 136 terminates at radiused ends 138 such that the parts 132 and 134 are biased away from each other to produce an expanded state when the safety probe is in the extended position. Use of the safety penetrating instrument of FIG. 9 for grasping and/or cutting tissue, for example for biopsy, is illustrated in FIG. 10 wherein it can be seen that tissue 140 can be grasped by placing the safety probe adjacent the tissue in the expanded state, as shown in FIG. 9, and, thereafter, pulling the safety probe proximally into the needle by manually grasping pin 78 and moving the pin along the longitudinal slot portion 82 against the bias of spring 80. The safety probe can be releasably locked in the retracted position by moving the pin 78 into transverse slot portion 86 and, into the recess 88 formed therein to prevent the pin from returning to its normally biased position. When the safety penetrating instrument is used for biopsy, the safety probe is preferably made of stainless steel and the distal edges are inwardly sharp to cut and grasp the tissue to be taken for biopsy.

Figure 11:
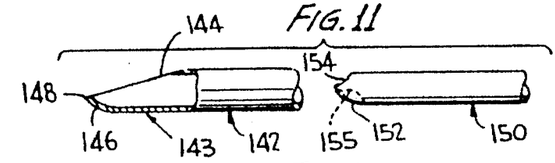
FIG. 11 is a broken, exploded view of another embodiment of the safety penetrating instrument according to the present invention.
Figure 12:
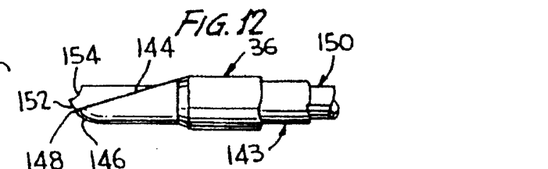
FIG. 12 is a broken side view of the safety penetrating instrument of FIG. 11 with the safety probe in an extended position.

Another embodiment of a safety penetrating instrument according to the present invention is illustrated in FIGS. 11 and 12 wherein an elongate tubular needle 142 has a distal end 143 with an open, acutely angled end defining a peripheral edge 144 with a portion 146 of the distal end curving toward the longitudinal axis of the needle to terminate at a sharp distal tip 148 laterally or radially displaced from the wall of the needle. A safety probe 150 has a distal end 152 with a curvature to protrude over sharp tip 148 when the safety probe is in the extended position as illustrated in FIG. 12. The distal end 152 has a bulbous configuration with an aperture 154 therein to permit communication through the safety penetrating instrument for injection or evacuation of fluid. While a smoothly curving configuration can provide protection for the sharp needle tip 148, a recess in the form of a concave portion 155 shown in dashed lines can be provided in the safety probe distal end to further prevent exposure of the sharp needle tip.

Figure 13:
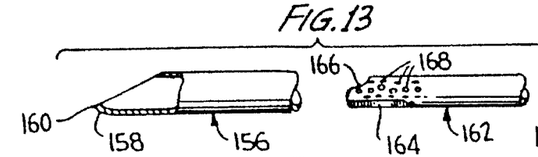
FIG. 13 is a broken, exploded view of another embodiment of the safety penetrating instrument according to the present invention.
Figure 14:
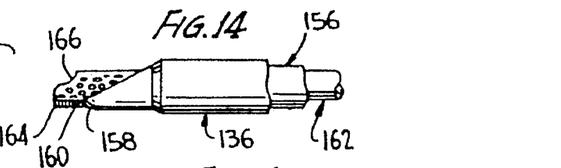
FIG. 14 is a broken side view of the modified safety penetrating instrument of FIG. 13 with the safety probe in an extended position.

Another embodiment of a safety penetrating instrument according to the present invention is illustrated in FIGS. 13 and 14 wherein an elongate tubular needle 156 has a curved distal portion 158 extending less then portion 146 shown in FIG. 11 to terminate at a sharp tip 160. A safety probe 162 has a longitudinal groove 164 therein to form a recess receiving the sharp needle tip 160 at the distal end of the needle as illustrated in FIG. 14. The distal end of the safety probe has a large hole 166 and a plurality of small holes 168 therein. By providing a plurality of holes in the distal end of the safety probe, communication can be maintained even if one of the holes becomes blocked.

Figure 15:
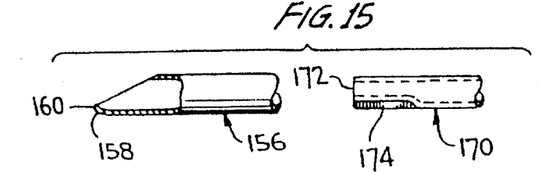
FIG. 15 is a broken, exploded view of another embodiment of the safety penetrating instrument according to the present invention.
Figure 16:
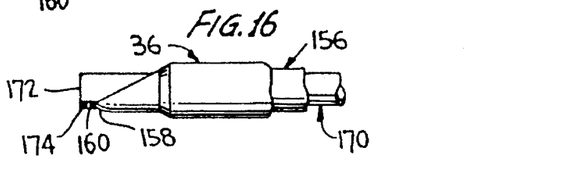
FIG. 16 is a broken side view of the safety penetrating instrument of FIG. 15 with the safety probe in an extended position.

The embodiment of a safety penetrating instrument according to the present invention illustrated FIGS. 15 and 16 is similar to that illustrated in FIGS. 13 and 14 with the exception that the safety probe 170 has an annular open distal end 172 allowing communication directly therethrough. The round peripheral edge of distal end 172 is interrupted to form a recess in the form of a slot or groove 174 for receiving the sharp needle tip 160.

Only the distal ends of the safety penetrating instrument have been illustrated in FIGS. 5–16; however, it will be appreciated that the proximal portions can be formed by any suitable cooperating structure and are particularly advantageous when utilized with the locking and spring biasing mechanism illustrated in FIGS. 1 and 2. Similarly, various features from the disclosed embodiments can be combined dependent upon the procedure to be performed with a particular safety penetrating instrument.

Figure 17:
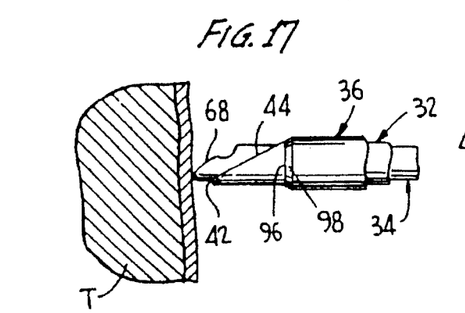
FIGS. 17, 18 and 19 are broken views illustrating use of the safety penetrating instrument of FIG. 1.
Figure 18:
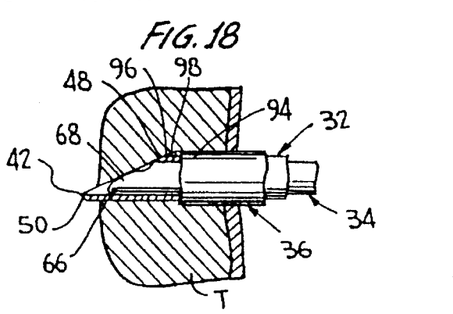

In use, it will be appreciated that with the pin 78 disposed in distal transverse slot portion 84, the safety probe cannot move proximally within needle 32 thereby assuring that the sharp tip 46 is protected to prevent inadvertent contact. When it is desired to penetrate an anatomical cavity, the blunt end surface 68 is positioned in abutment with the tissue T to be penetrated as illustrated in FIG. 17, and a finger is utilized to manually move pin 78 counter-clockwise against the torsional bias of spring 80 to be aligned with the longitudinal portion 82 of slot 60. With the pin 78 in this position, when the end surface 68 of the distal end of the safety probe is forced against the tissue to be penetrated, the safety probe 34 will move distally against the bias of spring 80 to the retracted position as illustrated in FIGS. 3 and 18, it being noted that when the distal end of the safety probe includes a bent or angled portion, the distal end of the safety probe will straighten out as the safety probe is withdrawn into the needle and additionally that when the distal end has an expanded state in the extended position the distal end will be in a contracted state when the safety probe distal end is moved to the retracted position. With the safety probe in the retracted position, penetration through the tissue with minimal tissue jamming and trapping is accomplished due to the smooth profile of the distal end of the safety penetrating instrument. Pin 78 will not enter proximal transverse slot portion 86 when the pin is aligned therewith due to the torsional or rotational bias of spring 80 in the opposite direction; and, thus, once the anatomical wall has been completely penetrated, spring 80 will bias the safety probe distally such that the safety probe returns to the extended position as illustrated in FIG. 19 to protect the sharp tip 46 such that the sharp tip is exposed only during the tissue penetrating step. When the safety probe includes a protective recess such as the groove 126 in the embodiment of FIG. 5, the bent or angled portions 130 in the embodiments of FIGS. 5 and 9, the slot 136 in the embodiment of FIG. 9, the concavity 154 in the embodiment of FIG. 11 and the grooves or slots 162 and 174 in the embodiments of FIGS. 13 and 15, the sharp needle tip is protected by being received in the recess. As previously noted, when the angle of the end surface of the safety probe distal end corresponds with the angle of the needle distal end, the distal ends of the needle and the safety probe will be disposed in substantially the same plane to reduce tissue resistance during penetrating and produce a minimum gap between the safety probe and the needle to minimize trapping or jamming of tissue therebetween. The reduction in tissue resistance is further enhanced by the positioning of the peripheral distal edge of the portal sleeve substantially in alignment with the trailing edge of the needle distal end. Protection of the sharp needle tip is particularly effective where the distal end of the needle is ground as shown at 50 in that the sharp needle tip will abut the distal end of the safety probe when the safety probe is in the extended position.

If, after penetration into the anatomical cavity, it is desired to penetrate additional tissue, the surgeon can selectively release the safety probe from the extended position by moving pin 78 counter-clockwise to be aligned with longitudinal slot portion 82. If the protection provided by the safety probe is not required or desired for further procedures, the pin 78 can be moved into recess 88 of proximal transverse slot portion 86 to releasably lock the safety probe in the retracted position or a position further withdrawn into needle 32 dependent upon the longitudinal position of transverse slot portion 86. If proximal transverse slot portion 90 is provided, the safety probe will automatically lock in the retracted position when pin 78 is aligned with slot portion 90 due to the rotational bias from spring 80. If slot portion 90 is positioned proximally of pin 78 when the safety probe is in the retracted position, the safety probe will not automatically lock during use but rather the pin will have to be manually pulled back to alignment with slot portion 90 to lock the safety probe within the needle.

While plate 76 and pin 78 can rotate slightly within hub 38, safety probe 34 does not rotate therewith to maintain alignment with needle 32, and various index configurations to maintain rotational alignment between the safety probe and the needle can be used, if desired. For example, the safety probe can be splined with the needle or with tube 64.

Once the safety penetrating instrument has penetrated into an anatomical cavity, the safety penetrating instrument can be used to permit flow of fluids into or out of the cavity since communication is established through hole 67 and the body of the safety probe 34 and through tube 64 and valve 62. In this manner, the safety penetrating instrument 30 can be used, for example, to create a pneumoperitoneum.

Once the needle has been used to penetrate tissue to the extent desired by the surgeon, the portal sleeve 36 can be left in place by withdrawing the penetrating unit from the portal unit; and, once the penetrating unit is withdrawn, valve member 108 will engage the valve seat formed by the distal edge of tube 110 to prevent fluid flow through the portal formed by the portal sleeve 36 and housing 40. If it is desired to then insert an instrument having a diameter less than the diameter of needle 32, adapter plug 114 is removed from the proximal end of tube 110 and replaced with an adapter plug having a central aperture and tubular passage formed by the inner wall 118 of a diameter corresponding to the smaller instrument to be inserted. It will be appreciated that the safety probe 34 alone can be withdrawn leaving the portal sleeve 36 and the needle 32 in place to conduct procedures, such as suction or irrigation, through the needle 32.

For procedures where it is desired to gain access to an area of an anatomical cavity substantially offset from the longitudinal axis of the safety penetrating instrument, the portal sleeve can have a normal, non-linear configuration such that, once penetration is completed and the penetrating unit is withdrawn from the portal unit, the portal sleeve will return to the non-linear configuration. For example, the portal sleeve is shown in dashed lines in FIG. 19 as having a curved configuration 181 to which the portal sleeve returns when the needle and safety probe are withdrawn.

A modification of the portal sleeve of the safety penetrating instrument is shown in FIG. 20 wherein the portal sleeve 36 has a distal end with a peripheral edge 176 obliquely arranged at an acute angle relative to the longitudinal axis of the needle with a rounded leading edge 178 disposed in longitudinal alignment with sharp needle tip 46 and a trailing edge 180 in alignment with the trailing edge 48 of the peripheral edge at the needle distal end. The modification of FIG. 20 has the advantages of assuring that at least the leading edge of the portal sleeve has penetrated the anatomical wall when the safety probe returns to the extended position and of facilitating; tissue penetration since the distal end of the portal sleeve gradually enters the tissue following the needle.

Another modification of the safety penetrating instrument of the present invention is shown in FIG. 21 wherein the valve assembly 106 is formed of a member 182 having an annular base 184 sealingly engaged with the distal end of tube 110 and a plurality of spaced, spreadable, legs 186 extending distally from base 184 to produce a normally conical configuration. The member 182 is preferably made of unitary construction of a material facilitating movement of medical instruments therethrough and allowing legs 186 to flex, such as a plastic like nylon. The legs 186 are concentrically disposed around annular base 184 and the central opening therethrough and are slightly spaced from each other and terminate at curved relief recesses (not shown). A conical, stretchable sleeve or membrane 188, preferably made of a rubber-like material such as silicone, has a configuration to tightly fit over legs 186 such that the sleeve and legs are normally biased to a closed position at the apex to prevent passage of fluids through the valve assembly. The valve assembly is normally biased to a closed position due to the elastic force of conical sleeve 188 around legs 186; and, when a surgical instrument is inserted through the portal unit, the surgical instrument will cause legs 186 to flex outwardly stretching conical sleeve 188 such that conical sleeve acts as a seal to prevent passage of fluids thereby and tightly engages the surgical instrument in the gaps where the legs are spread apart. The valve assembly provides a passage of variable size to accommodate surgical instruments of various sizes passing therethrough in that the legs and conical sleeve contract to sealingly engage the surgical instrument regardless of the diameter thereof, and, in combination with adapter plug 114, an excellent seal through the portal unit is established.

In the modification of FIG. 21, portal sleeve 36 is resiliently, movably secured to the housing 40 to allow the portal sleeve to be slightly moved with respect to the housing and the penetrating unit against a spring bias. The proximal end 190 of the portal sleeve slidably received in a nipple 192 which is threadedly secured to a front wall 193 of housing 40, and a seal is provided by one or more O-rings 194. The proximal end 190 carries an annular end collar 196 limiting distal movement-of the portal sleeve by abutment with the front wall portion of housing 40 formed by nipple 192. A helical spring 198 is mounted in compression between collar 196 and an annular shoulder 200 fixed in housing 40 such that the portal sleeve is distally biased. During penetration of tissue, the portal sleeve can move proximally against the bias of spring 198 to facilitate penetration during difficult procedures.

If automatic locking of the safety probe 34 in the extended position is not desired, the spring 80 is not wound during assembly such that pin 78 is not rotationally biased. Accordingly, after spring 80 returns the safety probe 34 to the extended position when the force on the safety probe distal end from tissue resistance is removed, the pin will not enter transverse slot portion 84, and the safety probe will not be locked in the extended position. Thus, the surgeon has the option of locking the safety probe in the extended position by manually moving pin 78 into transverse slot portion 84 or allowing the safety probe to be free to move proximally by not moving pin 78 into transverse slot portion 84.

Safety penetrating instruments formed of an elongate tubular needle with a safety probe having a distal end configured to define a protective recess for receiving the sharp tip of the needle in the extended position are particularly advantageous for safely introducing a portal sleeve into veins or arteries with reduction of the chances of developing hematoma. Where the safety penetrating instrument utilizes an elongate tubular needle with an acutely angled distal end including a portion curving toward the longitudinal axis of the needle to terminate at a sharp tip radially inwardly spaced from the wall of the needle and a safety probe having a distal end configured to protrude over the sharp tip in the extended position, rotational penetration can be safely performed to introduce a portal sleeve into the body. The distal end portion of the needle can be curved inwardly to any desired extent from a slight curve, as shown in FIGS. 11, 13 and 15, to a curve through almost the entire diameter of the needle to produce a sharp, spoon-like shape with the distal end of the safety probe configured to protrude over the sharp tip by providing a protective recess therein or by bending in the same direction as the curvature of the curved position.

The safety penetrating instrument of the present invention can be used for penetrating cavity walls in a manner similar to presently used trocars and can have various diameters ranging from 2 mm to 12 mm. The use of a tubular needle in the safety penetrating instrument of the present invention has the advantages of permitting placement of the portal sleeve or cannula in small or large cavities to provide a portal communicating therewith, of permitting a scooping movement during penetration to get through the wall without compressing the cavity when the needles of FIGS. 11, 13 and 15 are used, of being useful for first, second or other puncture techniques, of permitting penetration of a second cavity wall after penetration of a first cavity wall and of allowing the performance of additional procedural steps, such as suction, cutting, biopsy and aspiration. Dependent upon the configuration of the safety probe to be used and the procedure to be performed, the safety probe can be made of metal, such as stainless steel, rubber or plastic, with materials having good sliding characteristics, such as Teflon, being preferred. While the safety probes are advantageously hollow or tubular to allow passage of fluids therethrough, the safety probes can be solid if desired.

From the above, it will be appreciated that safety penetrating instruments according to the present invention provide increased protection of the sharp tip of a tubular needle while also facilitating use and tip exposure after penetration of an anatomical cavity by providing selective, releasable locking positions for the safety probe. It will be appreciated that the safety penetrating instrument of the present invention is useful to penetrate tissue in various portions of the body, and "anatomical cavity" as used herein refers to any area of the body requiring penetration of tissue for access.

Inasmuch as the present invention is subject to many variations, modifications and changes in detail, it is intended that all subject matter discussed above or shown in the accompanying drawings be interpreted as illustrative only and not to be taken in a limiting sense.

What is claimed is:

1. A safety penetrating instrument comprising
   an elongate penetrating member having a distal end defining a sharp tip for penetrating tissue;
   a safety member movably disposed relative to said penetrating member having a distal end and being movable between an extended position with said safety member distal end protruding distally from said penetrating member sharp tip and a retracted position with said safety member distal end disposed proximally of said penetrating member sharp tip to expose said penetrating member sharp tip;
   an elongate, tubular portal sleeve receiving said penetrating member and having a distal end disposed adjacent said penetrating member distal end;
   bias means for biasing said safety member toward said extended position and for permitting said safety member to move to said retracted position and returning said safety member to said extended position; and
   releasable locking means for automatically locking said safety member in said extended position after said safety member is returned to said extended position, said releasable locking means including means extending from said safety member for permitting said safety member to be pulled back from said extended position against the force from said bias means to expose said penetrating member sharp tip without requiring a force applied in a proximal direction to said safety member distal end.

2. A safety penetrating instrument as recited in claim 1 wherein said safety member is disposed at least partially within said penetrating member.

3. A safety penetrating instrument as recited in claim 2 wherein said penetrating member is a tubular needle having an open distal end and said safety member is a safety probe disposed within said tubular needle.

4. A safety penetrating instrument comprising an elongate penetrating member having a distal end defining a sharp tip for penetrating tissue;

a safety member disposed at least partially within said penetrating member and movably disposed relative to said penetrating member, said safety member having a distal end and being movable between an extended position with said safety member distal end protruding distally from said penetrating member sharp tip and a retracted position with said safety member distal end disposed proximally of said penetrating member sharp tip to expose said penetrating member shard tip;

hub means for mounting said penetrating member;

an elongate, tubular portal sleeve receiving said penetrating member and having a distal end disposed adjacent said penetrating member distal end;

bias means for biasing said safety member toward said extended position and for permitting said safety member to move to said retracted position and returning said safety member to said extended position; and releasable locking means for automatically locking said safety member in said extended position after said safety member is returned to said extended position, said releasable locking means including slot means disposed in said hub means and pin means coupled with said safety member and received in said slot means.

5. A safety penetrating instrument as recited in claim 4 wherein said penetrating member is a tubular needle having an open distal end and said safety member is a safety probe disposed within said tubular needle.

6. A safety penetrating instrument comprising an elongate penetrating member having a distal end defining a sharp tip for penetrating tissue;

a safety member disposed at least partially within said penetrating member and movably disposed relative to said penetrating member, said safety member having a distal end and being movable between an extended position with said safety member distal end protruding distally from said penetrating member sharp tip and a retracted position with said safety member distal end disposed proximally of said penetrating member sharp tip to expose said penetrating member sharp tip;

an elongate, tubular portal sleeve receiving said penetrating member and having a distal end disposed adjacent said penetrating member distal end;

bias means for biasing said safety member toward said extended position and for permitting said safety member to move to said retracted position and returning said safety member to said extended position; and releasable locking means for selectively locking said safety member in said retracted position.

7. A safety penetrating instrument as recited in claim 6 wherein said penetrating member is a tubular needle having an open distal end and said safety member is a safety probe disposed within said tubular needle.

8. A safety penetrating instrument comprising an elongate, hollow penetrating member having a longitudinal axis, a proximal end and a distal end with an opening therein disposed in a plane at an acute angle relative to said longitudinal axis, said penetrating member distal end terminating at a sharp tip for penetrating tissue;

a safety probe movably disposed in said penetrating member having a proximal end and a distal end terminating at an angled portion, said safety probe being movable between an extended position with said safety probe distal end protruding distally of said penetrating member tip and a retracted position with said angled portion of said safety probe distal end disposed substantially in said plane of said opening in said penetrating member distal end to expose said penetrating member tip;

hub means for receiving said proximal ends of said penetrating member and said safety probe;

housing means abutting said hub means;

bias means for biasing said safety probe toward said extended position and for permitting said safety probe to move to said retracted position in response to a proximally directed force applied to said safety probe distal end, said bias means returning said safety probe to said extended position when the force applied to said safety probe distal end is removed; and an elongate, tubular portal sleeve surrounding said penetrating member and having a distal end disposed adjacent said penetrating member distal end and a proximal end secured to said housing means.

9. A safety penetrating instrument as recited in claim 8 wherein said angled portion of said safety probe distal end is disposed substantially parallel with said plane of said opening in said penetrating member distal end in said extended position.

10. A safety penetrating instrument as recited in claim 8 wherein said angled portion of said safety probe distal end includes a substantially flat angled end surface and said angled end surface is disposed substantially in said plane of said opening in said penetrating member distal end in said retracted position to provide a smooth tissue penetrating surface.

11. A safety penetrating instrument comprising an elongate, hollow penetrating member having a longitudinal axis, a proximal end and a distal end with an opening therein disposed in a plane at an acute angle relative to said longitudinal axis, said penetrating member distal end terminating at a sharp tip for penetrating tissue;

a safety probe movably disposed in said penetrating member having a proximal end and a distal end terminating at an angled portion, said safety probe being movable between an extended position with said safety probe distal end protruding distally of said penetrating member tip and said angled portion of said safety probe distal end disposed substantially parallel with said plane of said opening in said distal end of said penetrating member and a retracted position with said safety probe distal end disposed in said opening in said distal end of said penetrating member to expose said penetrating member tip;

hub means for receiving said proximal ends of said penetrating member and said safety probe;

housing means abutting said hub means;

bias means for biasing said safety probe toward said extended position and for permitting said safety probe to move to said retracted position in response to a proximally directed force applied to said safety probe distal end, said bias means returning said safety probe to said extended position when the force applied to said safety probe distal end is removed; and an elongate, tubular portal sleeve surrounding said penetrating member and having a distal end disposed adjacent said penetrating member distal end and a proximal end secured to said housing means.

* * * * *